United States Patent
Kitahara

(10) Patent No.: US 11,684,340 B2
(45) Date of Patent: Jun. 27, 2023

(54) ULTRASOUND ENDOSCOPE

(71) Applicant: OLYMPUS CORPORATION, Tokyo (JP)

(72) Inventor: Toshihiro Kitahara, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 1296 days.

(21) Appl. No.: 15/841,512

(22) Filed: Dec. 14, 2017

(65) Prior Publication Data

US 2018/0168541 A1 Jun. 21, 2018

Related U.S. Application Data

(63) Continuation of application No. PCT/JP2016/060836, filed on Mar. 31, 2016.

(30) Foreign Application Priority Data

Jun. 23, 2015 (JP) .............................. JP2015-126052

(51) Int. Cl.
*A61B 8/12* (2006.01)
*A61B 1/00* (2006.01)
*A61B 8/00* (2006.01)

(52) U.S. Cl.
CPC ............ *A61B 8/12* (2013.01); *A61B 1/00096* (2013.01); *A61B 8/4483* (2013.01); *A61B 1/00082* (2013.01); *A61B 1/00174* (2013.01)

(58) Field of Classification Search
None
See application file for complete search history.

(56) References Cited

U.S. PATENT DOCUMENTS

| 5,191,890 A | 3/1993 | Hileman |
| 2004/0082883 A1* | 4/2004 | Kohno ................. A61B 8/4488 601/2 |

(Continued)

FOREIGN PATENT DOCUMENTS

| EP | 2 881 042 A1 | 6/2015 |
| JP | S62-227334 A | 10/1987 |

(Continued)

OTHER PUBLICATIONS

International Search Report dated Jun. 28, 2016 issued in International Application No. PCT/JP2016/060836.

(Continued)

*Primary Examiner* — Christopher Koharski
*Assistant Examiner* — Michael S Kellogg
(74) *Attorney, Agent, or Firm* — Scully, Scott, Murphy & Presser, P.C.

(57) ABSTRACT

An ultrasound endoscope includes: an insertion portion; an ultrasound functional unit including an ultrasound transducer; an endoscope functional unit that at least includes an imaging optical system; and a balloon locking portion configured to connect the ultrasound functional unit and the endoscope functional unit, the balloon locking portion having a groove shape that can lock a balloon. A first plane passes, in a direction of a longitudinal axis of the insertion portion, through a first end portion of the ultrasound transducer near the endoscope functional unit, the first plane being perpendicular to the longitudinal axis of the insertion portion, and the first plane is positioned closer to a proximal end than a second plane passing through a second end portion of the balloon locking portion near the ultrasound functional unit, the second plane being perpendicular to the longitudinal axis of the insertion portion.

18 Claims, 7 Drawing Sheets

(56) References Cited

U.S. PATENT DOCUMENTS

| | | | |
|---|---|---|---|
| 2008/0051655 A1* | 2/2008 | Sato | A61B 1/00039 |
| | | | 600/439 |
| 2008/0188756 A1* | 8/2008 | Fujimura | A61B 8/445 |
| | | | 600/459 |
| 2009/0088646 A1* | 4/2009 | Nagano | A61B 8/00 |
| | | | 600/463 |
| 2013/0137990 A1* | 5/2013 | Tsuruta | A61B 1/00087 |
| | | | 600/466 |
| 2013/0184732 A1* | 7/2013 | Tanaka | A61B 10/04 |
| | | | 606/185 |
| 2013/0204140 A1* | 8/2013 | Irie | A61B 1/0011 |
| | | | 600/459 |
| 2013/0218018 A1 | 8/2013 | Kurihara | |
| 2013/0223193 A1* | 8/2013 | Takahashi | B06B 1/0622 |
| | | | 367/140 |

FOREIGN PATENT DOCUMENTS

| | | |
|---|---|---|
| JP | 2004-254942 A | 9/2004 |
| JP | 2007-135949 A | 6/2007 |
| JP | 2011-206416 A | 10/2011 |
| JP | 2012-245061 A | 12/2012 |
| JP | 2013-027695 A | 2/2013 |
| WO | 92/18054 A1 | 10/1992 |

OTHER PUBLICATIONS

Extended Supplementary European Search Report dated Nov. 2, 2018 in European Patent Application No. 16 81 4021.8.

* cited by examiner

ULTRASOUND ENDOSCOPE

CROSS-REFERENCE TO RELATED APPLICATION

This application is a continuation of PCT international application Ser. No. PCT/JP2016/060836 filed on Mar. 31, 2016 which designates the United States, incorporated herein by reference, and which claims the benefit of priority from Japanese Patent Applications No. 2015-126052, filed on Jun. 23, 2015, incorporated herein by reference.

BACKGROUND

The present disclosure relates to an ultrasound endoscope.

For observing the property of body tissue or material that is an observation target, ultrasound waves are applied in some cases. More particularly, an ultrasound observation apparatus can acquire information related to the property of the observation target, by performing predetermined signal processing on an ultrasound echo received from an ultrasound transducer that transmits and receives ultrasound waves.

The ultrasound transducer includes a plurality of piezoelectric elements that converts an electrical pulse signal into an ultrasound pulse (acoustic pulse), emits the ultrasound pulse onto the observation target, converts the ultrasound echo reflected by the observation target, into an electrical echo signal, and outputs the electrical echo signal. For example, by arranging a plurality of piezoelectric elements along a predetermined direction, and electrically switching an element involved in the transmission and reception, or delaying the transmission and reception of each element, an ultrasound echo is acquired from the observation target.

There are known a plurality of types of ultrasound transducers having different ultrasound-beam transmission and reception directions, such as a convex type, a linear type, and a radial type. Among these types, for example as disclosed in JP 2004-254942 A, a convex-type ultrasound transducer includes a plurality of piezoelectric elements arrayed along a curved surface, and each element emits an ultrasound beam in a radial direction of the curved surface. JP 2004-254942 A discloses a configuration in which a convex-type ultrasound transducer is provided at a distal end of an insertion portion of an ultrasound endoscope.

SUMMARY

An ultrasound endoscope according to one aspect of the present disclosure includes: an insertion portion to be inserted into a subject; an ultrasound functional unit provided at a distal end of the insertion portion, the ultrasound functional unit including an ultrasound transducer configured to transmit and receive an ultrasound wave on a surface including a longitudinal axis of the insertion portion, the surface being parallel to the longitudinal axis; and an endoscope functional unit connected to the ultrasound functional unit, the endoscope functional unit at least including: a balloon locking portion having a groove shape that can lock a balloon; and an imaging optical system, wherein a first plane passes, in a direction of the longitudinal axis of the insertion portion, through an end portion of the ultrasound transducer near the endoscope functional unit, the first plane being perpendicular to the longitudinal axis of the insertion portion, and the first plane is positioned closer to a proximal end than a second plane passing through an end portion of the endoscope functional unit near the ultrasound functional unit, the end portion of the endoscope functional unit being a boundary between the ultrasound functional unit and the endoscope functional unit.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments will be described below with reference to the drawings. In addition, the present disclosure is not limited by the embodiment to be described below. Furthermore, in the description of the drawings, the same parts are assigned the same signs.

First Embodiment

Figure 1:
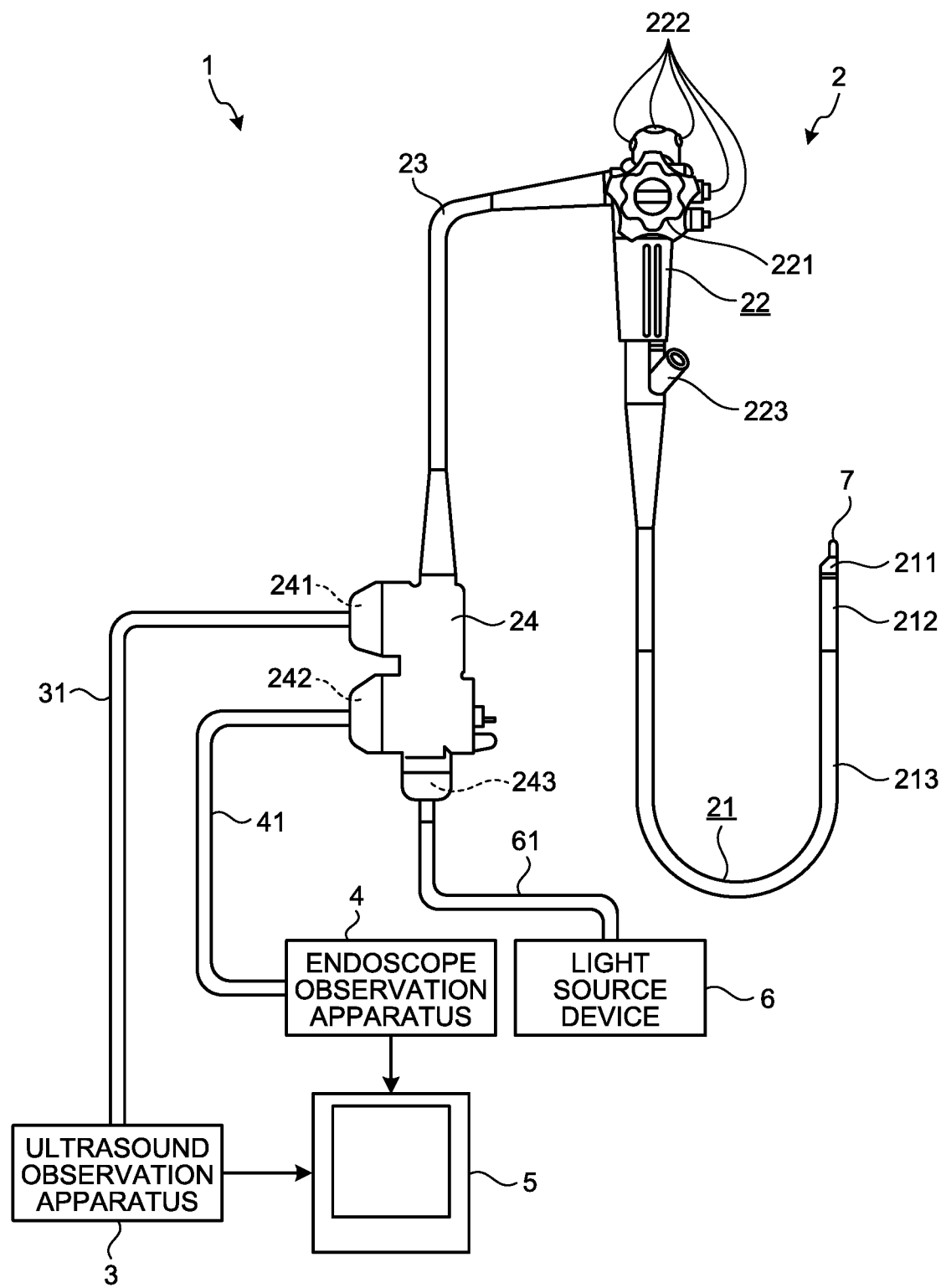
FIG. 1 is a diagram schematically illustrating an endoscope system according to a first embodiment.

FIG. 1 is a diagram schematically illustrating an endoscope system according to a first embodiment. An endoscope system 1 is a system for performing ultrasound diagnosis of the inside of a subject such as a human, using an ultrasound endoscope. As illustrated in FIG. 1, the endoscope system 1 includes an ultrasound endoscope 2, an ultrasound observation apparatus 3, an endoscope observation apparatus 4, a display device 5, and a light source device 6.

The ultrasound endoscope 2 converts an electrical pulse signal received from the ultrasound observation apparatus 3, into an ultrasound pulse (acoustic pulse), emits the ultrasound pulse onto a subject at its distal end portion, converts an ultrasound echo reflected by the subject, into an electrical echo signal represented by voltage change, and outputs the electrical echo signal.

The ultrasound endoscope 2 includes an imaging optical system and an image sensor, is inserted into a digestive tract (esophagus, stomach, duodenum, large intestine) or a respiratory organ (trachea, bronchus) of the subject, and can perform capturing of the digestive tract or the respiratory organ. In addition, their adjacent organs (pancreas, cholecystis, biliary duct, biliary tract, lymph nodes, mediastinum organ, blood vessels, etc.) can be captured using ultrasound waves. In addition, the ultrasound endoscope 2 includes a light guide that guides illumination light to be emitted onto a subject when optical capturing is performed. The light guide has a distal end portion and a proximal end portion. The distal end portion reaches a distal end of an insertion portion to be inserted into a subject of the ultrasound endoscope 2. On the other hand, the proximal end portion is connected to the light source device 6 that generates illumination light.

As illustrated in FIG. 1, the ultrasound endoscope 2 includes an insertion portion 21, an operating unit 22, a universal cord 23, and a connector 24. The insertion portion 21 is a portion to be inserted into the subject. As illustrated in FIG. 1, the insertion portion 21 includes a rigid distal end portion 211 that is provided on a distal end side, and holds a ultrasound transducer 7, a curve portion 212 capable of curving that is connected to a proximal end side of the distal end portion 211, and a flexible tube portion 213 having flexibility that is connected to a proximal end side of the curve portion 212. Here, inside the insertion portion 21, a light guide for transferring illumination light supplied from the light source device 6, and a plurality of signal cables for transferring various signals are laid, and a processing tool insertion path for inserting a processing tool is formed, of which specific illustrations are omitted in the drawings. In addition, in the specification, the ultrasound transducer 7 side of the insertion portion 21 will be referred to as a distal end (also referred to as one end in a longitudinal axis N (refer to FIG. 4) direction of the insertion portion 21), and a side connecting to the operating unit 22 will be referred to as a proximal end (also referred to as another end in the longitudinal axis N direction of the insertion portion 21).

The ultrasound transducer 7 may be any of a convex transducer and a linear transducer. In the first embodiment, the description will be given assuming that the ultrasound endoscope 2 electrically performs scanning by providing, as the ultrasound transducer 7, a plurality of piezoelectric elements in an array, and electrically switching a piezoelectric element involved in transmission and reception, or delaying transmission and reception of each piezoelectric element. Nevertheless, the ultrasound endoscope 2 may mechanically scan the ultrasound transducer 7. A configuration of the ultrasound transducer 7 will be described later.

Figure 2:
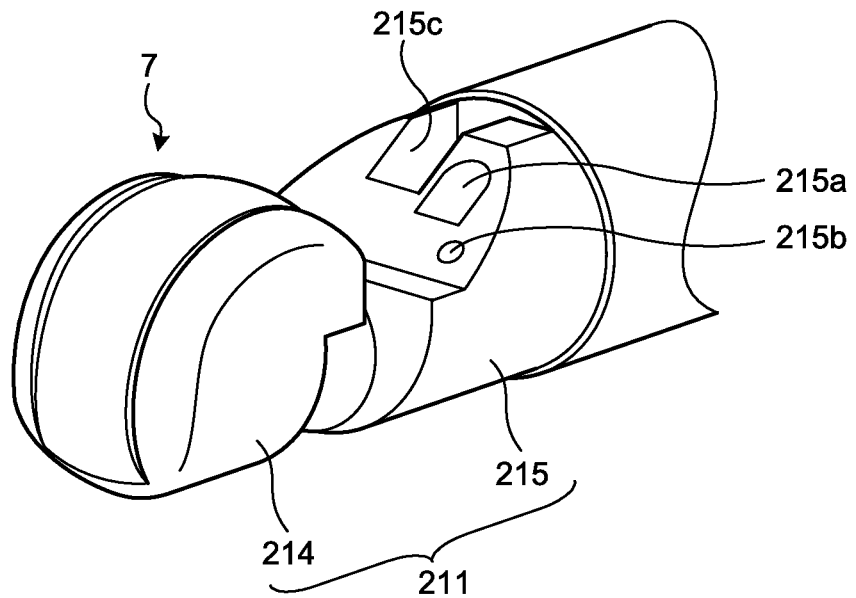
FIG. 2 is a perspective view schematically illustrating a distal end configuration of an insertion portion of an ultrasound endoscope according to the first embodiment.
Figure 3:
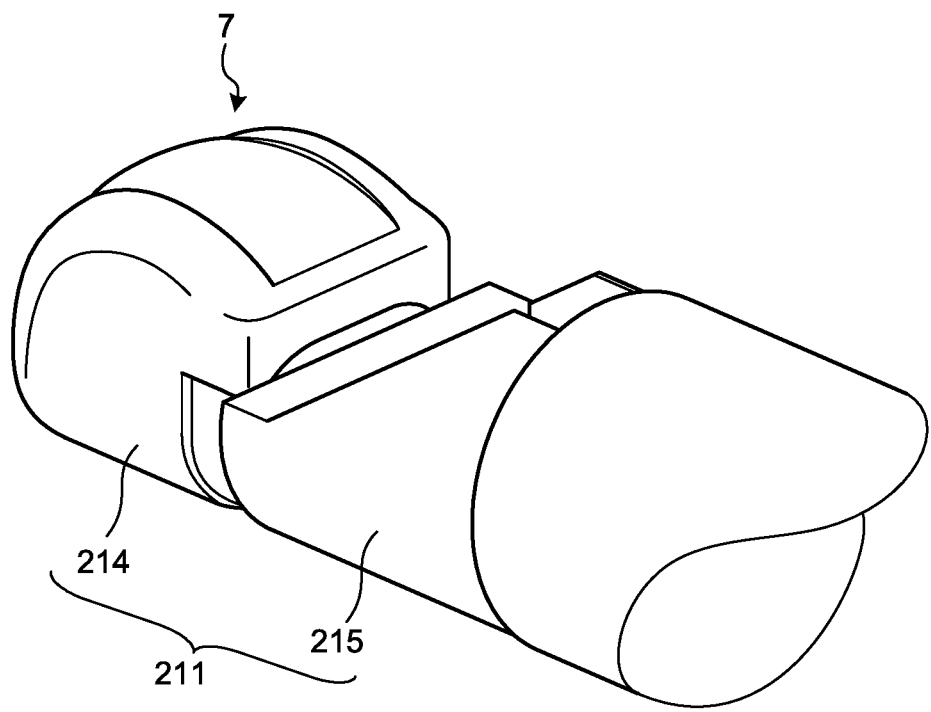
FIG. 3 is a perspective view schematically illustrating a distal end configuration of the insertion portion of the ultrasound endoscope according to the first embodiment.

FIG. 2 is a perspective view schematically illustrating a distal end configuration of the insertion portion of the ultrasound endoscope according to the first embodiment. FIG. 3 is a perspective view schematically illustrating a distal end configuration of the insertion portion of the ultrasound endoscope according to the first embodiment, and is a perspective view of the distal end configuration of the insertion portion that is viewed from an opposite direction to FIG. 2. As illustrated in FIG. 2, the distal end portion 211 includes an ultrasound functional unit 214 that holds the ultrasound transducer 7, and an endoscope functional unit 215 including an observation window 215a that causes light to enter an imaging optical system that includes an objective lens and the like, and takes in light from the outside, and an illumination window 215b being a part of an illumination optical system that collects illumination light and emits the illumination light to the outside. In the endoscope functional unit 215, a processing tool protrusion port 215c that is communicated with the processing tool insertion path formed in the insertion portion 21, and causes a processing tool to protrude from the distal end of the insertion portion 21 is formed. The endoscope functional unit 215 detachably connects with the ultrasound functional unit 214 at one end, and connects to the curve portion 212 at another end. The processing tool insertion path is provided so that an end vicinity connecting to the processing tool protrusion port 215c inclines with respect to the longitudinal axis N of the insertion portion 21, and the processing tool protrudes from the processing tool protrusion port 215c in a direction inclining with respect to the longitudinal axis N. The longitudinal axis N here refers to an axis extending along the longitudinal direction of the insertion portion 21. In the curve portion 212 and the flexible tube portion 213, an axis direction varies depending on each position. Nevertheless, in the rigid distal end portion 211, the longitudinal axis N is an axis forming a fixed straight line.

The operating unit 22 is a portion that is connected to a proximal end side of the insertion portion 21, and receives various operations from a doctor or the like. As illustrated in FIG. 1, the operating unit 22 includes a curve knob 221 for performing a curving operation of the curve portion 212, and a plurality of operating members 222 for performing various operations. In addition, a processing tool insertion port 223 that is communicated with the processing tool insertion path, and is provided for inserting the processing tool into the processing tool insertion path is formed in the operating unit 22.

The universal cord 23 is a cable extending from the operating unit 22, and in which a plurality of signal cables for transferring various signals, optical fibers for transferring illumination light supplied from the light source device 6, and the like are laid.

The connector 24 is provided at a distal end of the universal cord 23. In addition, the connector 24 includes first to third connector portions 241 to 243 to which an ultrasound cable 31, a video cable 41, and an optical fiber cable 61 are respectively connected.

The ultrasound observation apparatus 3 electrically-connects to the ultrasound endoscope 2 via the ultrasound cable 31 (FIG. 1), outputs a pulse signal to the ultrasound endoscope 2 via the ultrasound cable 31, and inputs an echo signal from the ultrasound endoscope 2. Then, the ultrasound observation apparatus 3 performs predetermined processing on the echo signal to generate an ultrasound image.

The endoscope observation apparatus 4 electrically-connects to the ultrasound endoscope 2 via the video cable 41 (FIG. 1), and inputs an image signal from the ultrasound endoscope 2 via the video cable 41. Then, the endoscope observation apparatus 4 performs predetermined processing on the image signal to generate an endoscope image.

The display device 5 is formed by using a liquid crystal, an organic electro luminescence (EL), a projector, a cathode ray tube (CRT), or the like, and displays the ultrasound image generated in the ultrasound observation apparatus 3, the endoscope image generated in the endoscope observation apparatus 4, and the like.

The light source device 6 connects to the ultrasound endoscope 2 via the optical fiber cable 61 (FIG. 1), and supplies, via the optical fiber cable 61, illumination light for illuminating the inside of a subject, to the ultrasound endoscope 2.

Figure 4:
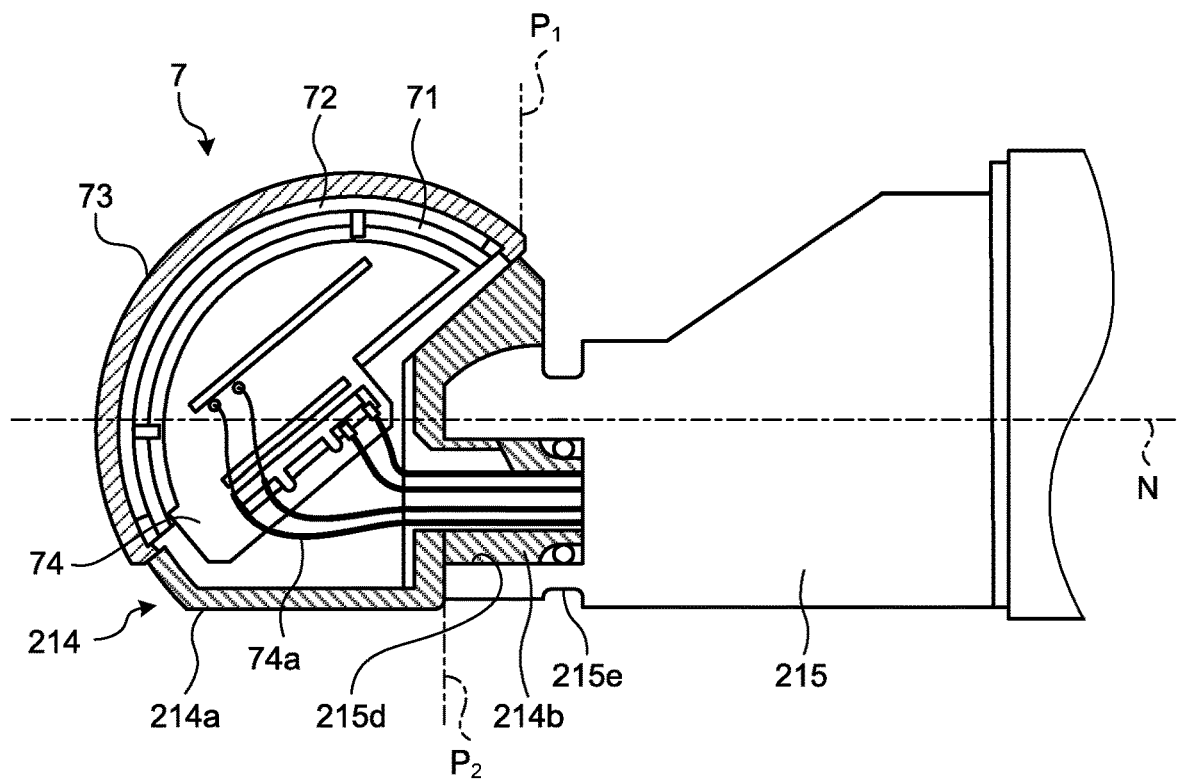
FIG. 4 is a partially-enlarged view schematically illustrating a configuration of an ultrasound functional unit according to the first embodiment.

Subsequently, a configuration of the ultrasound transducer 7 provided at the distal end of the insertion portion 21 will be described with reference to FIGS. 2 to 4. FIG. 4 is a partially-enlarged view schematically illustrating a configuration of the ultrasound functional unit according to the first embodiment, and is a partially-enlarged view in which a plane passing through the longitudinal axis of the insertion portion 21 is assumed to be a cutting plane. In the first embodiment, the description will be given assuming that the ultrasound transducer 7 is a convex-type ultrasound transducer as illustrated in FIG. 2, and is a one-dimensional array (1D array) having a piezoelectric element group 71 in which a plurality of piezoelectric elements is arrayed in a line. In other words, in the ultrasound transducer 7 according to the first embodiment, the plurality of piezoelectric elements 71 is arranged along an outer surface forming a curved surface of the ultrasound transducer 7, and transmits and receives ultrasound waves on a surface including the longitudinal axis N and being parallel to the longitudinal axis N.

The ultrasound transducer 7 includes the piezoelectric element group 71 having a prismatic shape, and including a plurality of piezoelectric elements arranged with a uniform longitudinal direction, an acoustic matching layer 72 each provided on the outer surface side of the ultrasound transducer 7 for the piezoelectric element group 71, an acoustic lens 73 provided on an opposite side to the side of the acoustic matching layer 72 that is in contact with the piezoelectric element group 71, a relay board 74 that electrically connects each piezoelectric element of the piezoelectric element group 71, and a cable into which the insertion portion 21 is inserted, and a backing material (not illustrated) provided on an opposite side to a side of the piezoelectric element group 71 that is in contact with the acoustic matching layer 72 (refer to FIG. 4). The backing material fills a hollow space formed between the acoustic matching layer 72 and a wall portion having a cup shape and accommodating the relay board 74. A cable 74a into which the insertion portion 21 is to be inserted is connected to the relay board 74.

The piezoelectric element converts an electrical pulse signal into an ultrasound pulse (acoustic pulse), emits the ultrasound pulse onto a subject, converts an ultrasound echo reflected by the subject, into an electrical echo signal represented by a voltage change, and outputs the electrical echo signal.

The acoustic matching layer 72 matches acoustic impedance between a piezoelectric element and an observation target for efficiently transmitting sound (ultrasound waves) between the piezoelectric element group 71 and the observation target. The acoustic matching layer 72 may be formed of a plurality of layers made of materials different from each other, or may be one layer depending on the properties of the piezoelectric element and the observation target.

The acoustic lens 73 covers the acoustic matching layer 72 and the outer surface of the wall portion. The acoustic lens 73 constitutes a part of the outer surface of the ultrasound transducer 7. The acoustic lens 73 is formed by using silicone, polymethylpentene, epoxy resin, polyetherimide, and the like. One surface of the acoustic lens 73 has a convex shape or a concave shape so as to have a function of stopping down ultrasound waves. The acoustic lens 73 emits ultrasound waves having passed through the acoustic matching layer 72, to the outside, or takes in an ultrasound echo from the outside. The acoustic lens 73 can be arbitrarily provided, and a configuration not including the acoustic lens 73 may be employed.

The backing material attenuates unnecessary ultrasound vibration generated by an operation of the piezoelectric element. The backing material is formed by using material having a large attenuation rate, such as, for example, epoxy resin in which fillers such as alumina and zirconia are dispersed, or rubber in which the aforementioned fillers are dispersed.

As mentioned above, the ultrasound functional unit 214 detachably connects with the endoscope functional unit 215. More particularly, the ultrasound functional unit 214 includes a main body portion 214a that holds the ultrasound transducer 7, and a protrusion portion 214b that protrudes from the main body portion 214a, and connects with the endoscope functional unit 215. In contrast to this, the endoscope functional unit 215 includes a hole portion 215d that is provided at an end portion on the opposite side to a side connecting with the curve portion 212, and is a hole connecting with the ultrasound functional unit 214, and a balloon locking portion 215e having a groove shape that can lock a balloon (not illustrated). The ultrasound functional unit 214 and the endoscope functional unit 215 connect to each other by the protrusion portion 214b fitting into the hole portion 215d. At this time, both units may be fixed by a known method such as adhesive agent and screwing.

The ultrasound transducer 7 having the above configuration emits ultrasound waves onto an observation target via the acoustic matching layer 72 and the acoustic lens 73 by each piezoelectric element vibrating according to an input of a pulse signal. At this time, in the piezoelectric elements, on an opposite side to an arrangement side of the acoustic matching layer 72 and the acoustic lens 73, due to the backing material, vibration of the piezoelectric elements is attenuated, and the vibration of the piezoelectric elements is not transmitted. In addition, ultrasound waves reflected by the observation target are transmitted to each piezoelectric element via the acoustic matching layer 72 and the acoustic lens 73. The piezoelectric element vibrates according to the transmitted ultrasound waves, and the piezoelectric element converts the vibration into an electrical echo signal, and outputs, as an echo signal, the electrical echo signal to the ultrasound observation apparatus 3 via a cable (not illustrated).

Subsequently, the arrangement of the ultrasound transducer 7 in the ultrasound functional unit 214 will be described with reference to FIG. 4. As illustrated in FIG. 4, a plane $P_1$ (first plane) passes, in the longitudinal axis N direction of the insertion portion 21, through an end portion of the ultrasound transducer 7 near the endoscope functional unit 215 and is perpendicular to the longitudinal axis N of the insertion portion 21. The plane $P_1$ is positioned closer to a proximal end than a plane $P_2$ (second plane) passing through an end portion of the hole portion 215d near the ultrasound functional unit 214, the end portion being an end portion of the endoscope functional unit 215 and being a boundary between the ultrasound functional unit 214 and the endoscope functional unit 215.

For example, in the case of increasing a curvature radius of a curved surface of the ultrasound transducer 7 (curved surface passing through distal ends of a plurality of piezoelectric elements) without changing the size and the number of piezoelectric elements, even if the ultrasound transducer 7 upsizes, if an end portion on the proximal end side of the ultrasound transducer 7 is extended toward the proximal end side in the longitudinal axis N direction of the insertion portion 21 so as to satisfy a positional relationship with the plane $P_1$ and the plane $P_2$, without elongating an end portion on the distal end side of the ultrasound transducer 7, even if the ultrasound transducer 7 upsizes, the insertion portion 21 can be formed without elongating an extension length in the longitudinal axis direction of the insertion portion 21.

Figure 5:
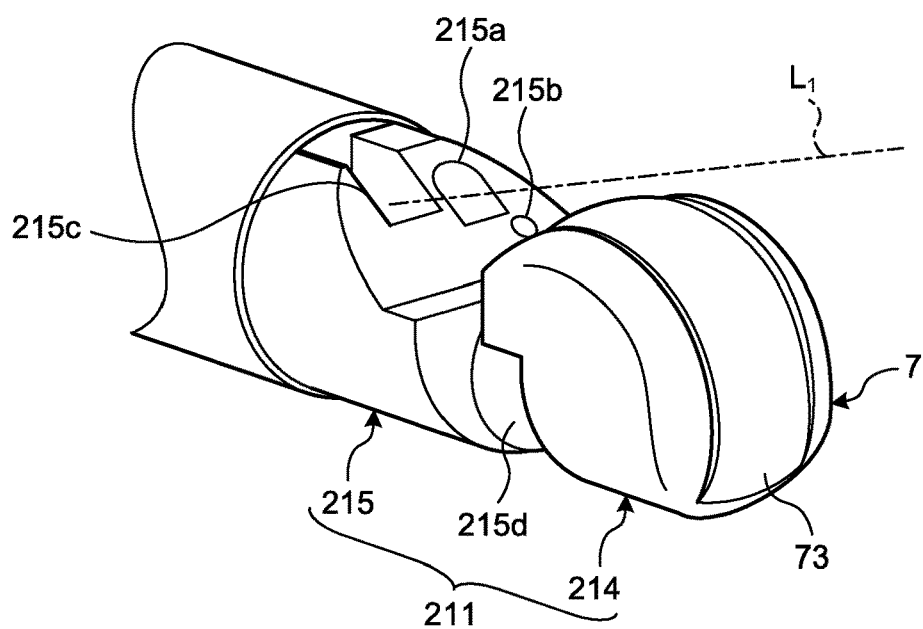
FIG. 5 is a perspective view schematically illustrating a distal end configuration of the insertion portion of the ultrasound endoscope according to the first embodiment.

FIG. 5 is a perspective view schematically illustrating a distal end configuration of the insertion portion of the ultrasound endoscope according to the first embodiment. As illustrated in FIG. 5, the outer surface of the ultrasound transducer 7 does not interfere with an axis $L_1$ extending in an extending direction of the processing tool protruding from the processing tool protrusion port 215c. Thus, if the ultrasound transducer 7 satisfies the aforementioned positional relationship with the plane $P_1$ and the plane $P_2$, the ultrasound transducer 7 does not interfere with an operation of the processing tool protruding from the processing tool protrusion port 215c.

Figure 6:
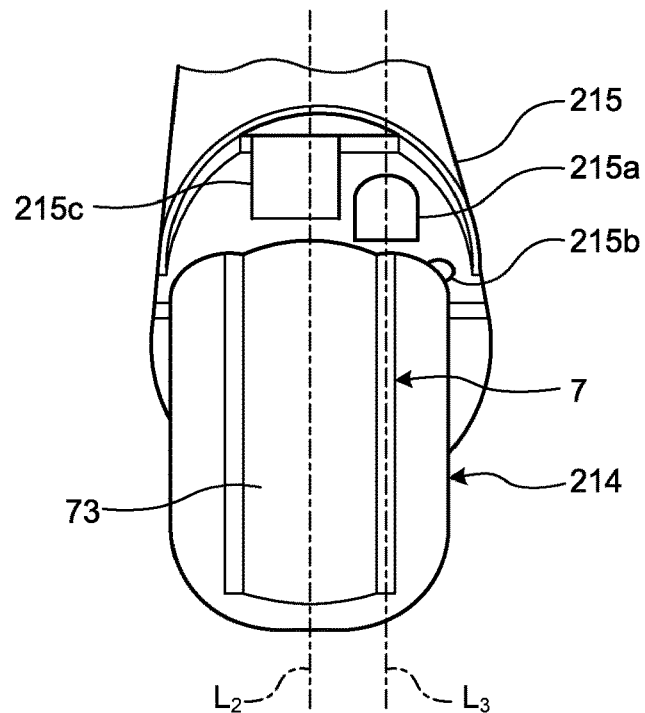
FIG. 6 is a plan view schematically illustrating a configuration of the insertion portion of the ultrasound endoscope according to the first embodiment that is viewed from a distal end side.

FIG. 6 is a plan view schematically illustrating a configuration of the insertion portion of the ultrasound endoscope according to the first embodiment that is viewed from a distal end side. As illustrated in FIG. 6, an axis $L_2$ passing through the center of the ultrasound transducer 7 in a direction perpendicular to the longitudinal axis direction of the insertion portion 21, and being parallel to the longitudinal axis direction of the insertion portion 21 is offset with respect to an axis $L_3$ passing through the center of the observation window 215a, and being parallel to the longitudinal axis direction of the insertion portion 21. Thus, for example, even if the outer surface of the acoustic lens 73 forms a convex shape along a direction perpendicular to the longitudinal axis direction of the insertion portion 21, the ultrasound transducer 7 does not interfere with light entering the observation window 215a.

Figure 7:
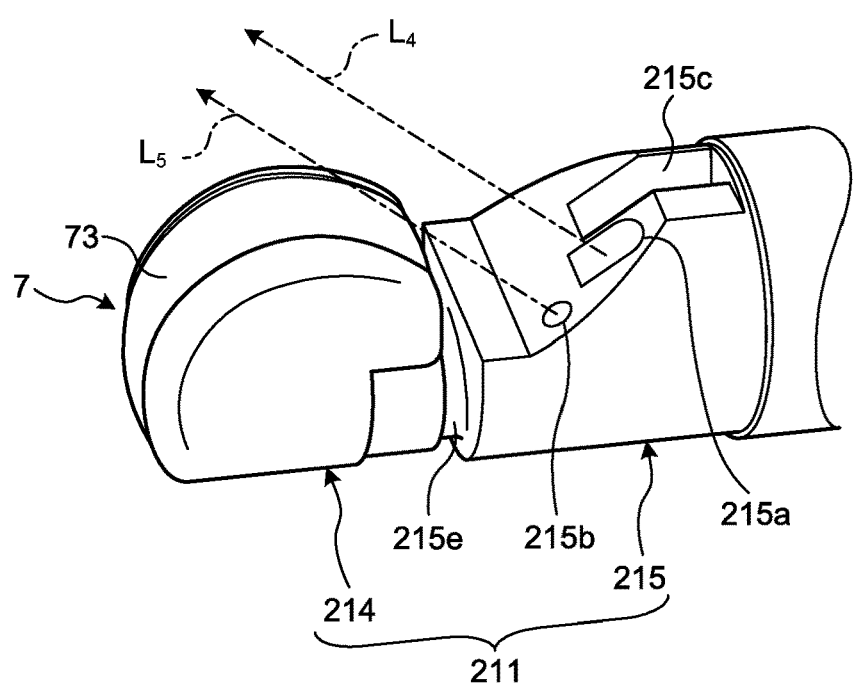
FIG. 7 is a perspective view schematically illustrating a distal end configuration of the insertion portion of the ultrasound endoscope according to the first embodiment.

FIG. 7 is a perspective view schematically illustrating a distal end configuration of the insertion portion of the ultrasound endoscope according to the first embodiment. As illustrated in FIG. 7, the outer surface of the ultrasound transducer 7 does not interfere with an optical axis $L_4$ (imaging optical axis of imaging optical system) of light entering the observation window 215a, and an optical axis $L_5$ of illumination light emitted by the illumination window 215b constituting a part of the illumination optical system. Thus, if the ultrasound transducer 7 satisfies the aforementioned positional relationship with the plane $P_1$ and the plane $P_2$, the ultrasound transducer 7 does not interfere with observation light entering the imaging optical system, and illumination light emitted from the illumination window 215b.

According to the first embodiment described above, in the longitudinal axis direction of the insertion portion 21, the plane $P_1$ passing through an end portion on the endoscope functional unit 215 side of the ultrasound transducer 7, and being perpendicular to the longitudinal axis of the insertion portion 21 is positioned on the proximal end side of the plane $P_2$ passing through an end portion of the endoscope functional unit 215 that serves as a boundary between the ultrasound functional unit 214 and the endoscope functional unit 215, and is an end portion on the ultrasound functional unit 214 side of the hole portion 215d. Thus, a curvature radius of the ultrasound transducer 7 can be increased without elongating an extension length of the ultrasound transducer 7, and without causing upsizing.

In addition, in the aforementioned first embodiment, the description has been given using the 1D array as an example. Alternatively, a 1.25D array, 1.5D array, 1.75D array, and the like, in which a plurality of piezoelectric elements (vibration portions) is arrayed in a direction (elevation direction) substantially-perpendicular to a scanning direction of the ultrasound transducer (an array direction of the piezoelectric elements in the 1D array), can also be applied. In addition, in the first embodiment, 1.25D, 1.5D, and 1.75D that are divided in the elevation direction, and acquire one ultrasound image in the scanning direction are included assuming that a plurality of piezoelectric elements is one-dimensionally arrayed.

In addition, in the aforementioned first embodiment, the description has been given assuming that the ultrasound functional unit 214 and the endoscope functional unit 215 are separate units. Nevertheless, if the aforementioned positional relationship with the plane $P_1$ and the plane $P_2$ is satisfied, the units may be integrally provided.

Modified Example of First Embodiment

Figure 8:
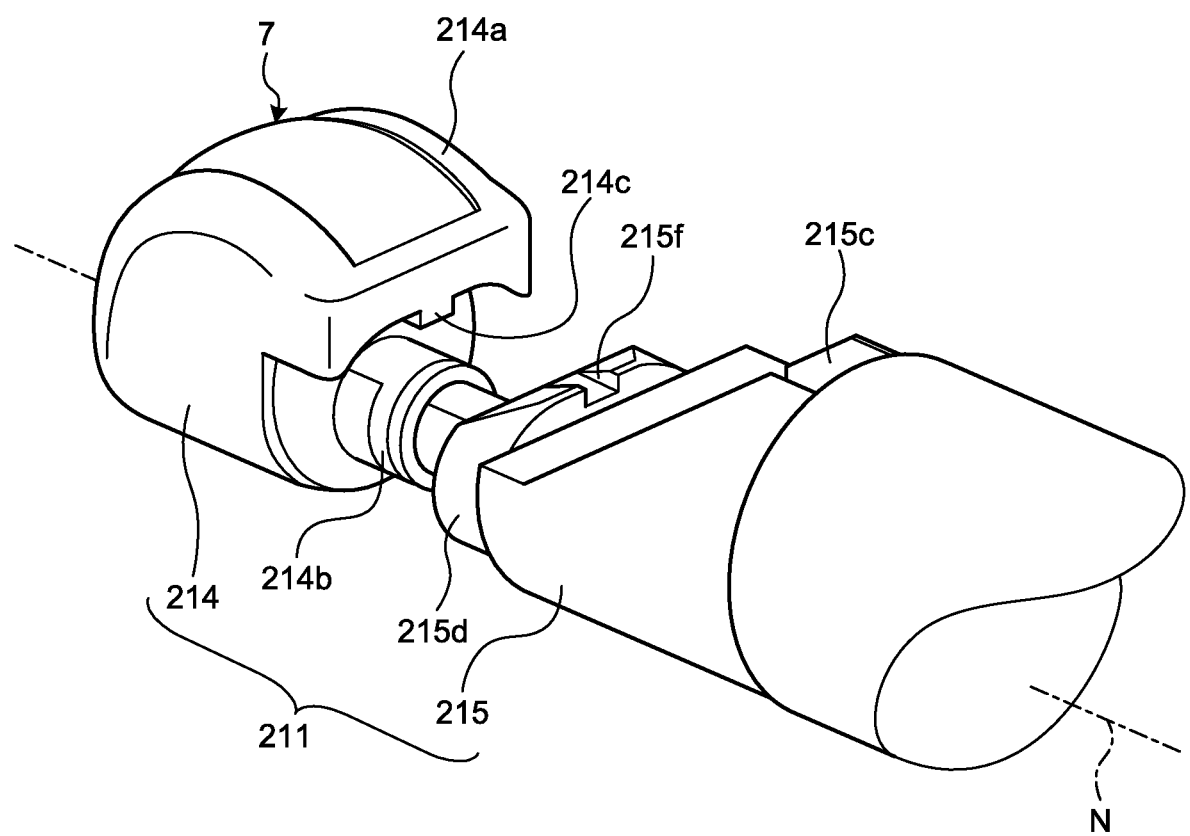
FIG. 8 is a perspective view schematically illustrating a distal end configuration of an insertion portion of an ultrasound endoscope according to a modified example of the first embodiment.

FIG. 8 is a perspective view schematically illustrating a distal end configuration of an insertion portion of an ultrasound endoscope according to a modified example of the first embodiment. In this modified example, the main body portion 214a according to the aforementioned first embodiment is provided with a projection portion 214c, and a recessed portion 215f is provided on an outer circumferential surface of the hole portion 215d.

More particularly, the projection portion 214c is provided at an end portion of the main body portion 214a on a side connecting with the endoscope functional unit 215. In addition, the recessed portion 215f is provided on a surface that is the outer circumferential surface of the hole portion 215d, and is in contact with the ultrasound functional unit 214, according to a formation position of the projection portion 214c. The projection portion 214c can fit into the recessed portion 215f, and at least a side surface in a direction rotating around the longitudinal axis of the insertion portion 21 fits thereinto with being in contact with a wall surface of the recessed portion 215f.

According to this modified example, the main body portion 214a is provided with the projection portion 214c, and the recessed portion 215f is provided on the outer circumferential surface of the hole portion 215d, and the projection portion 214c fits into with being in contact with the wall surface of the recessed portion 215f, at least on the side surface in the direction rotating around the axis N being parallel to the longitudinal axis of the insertion portion 21. Thus, the ultrasound functional unit 214 and the endoscope functional unit 215 can be relatively positioned, and the ultrasound functional unit 214 can suppress the rotation around the longitudinal axis of the insertion portion 21.

Second Embodiment

Figure 9:
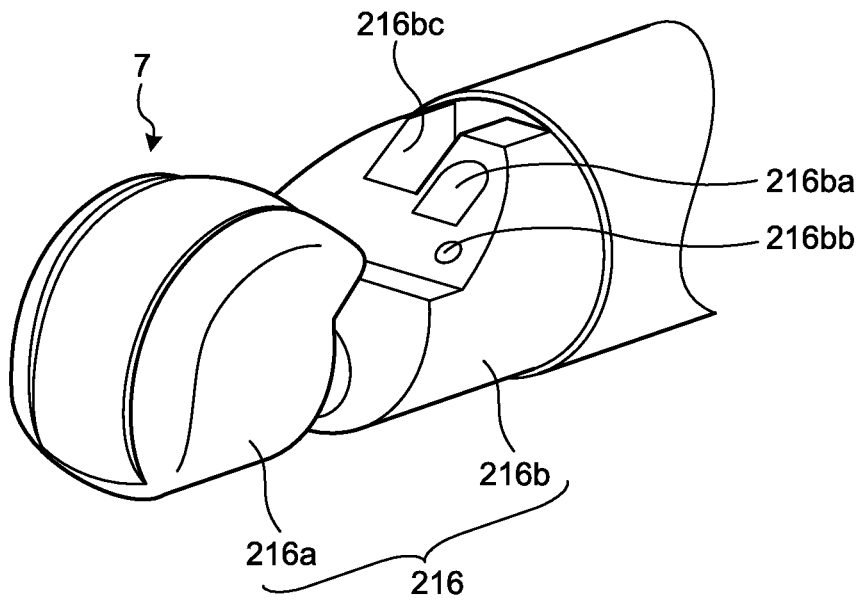
FIG. 9 is a perspective view schematically illustrating a distal end configuration of an insertion portion of an ultrasound endoscope according to a second embodiment.
Figure 10:
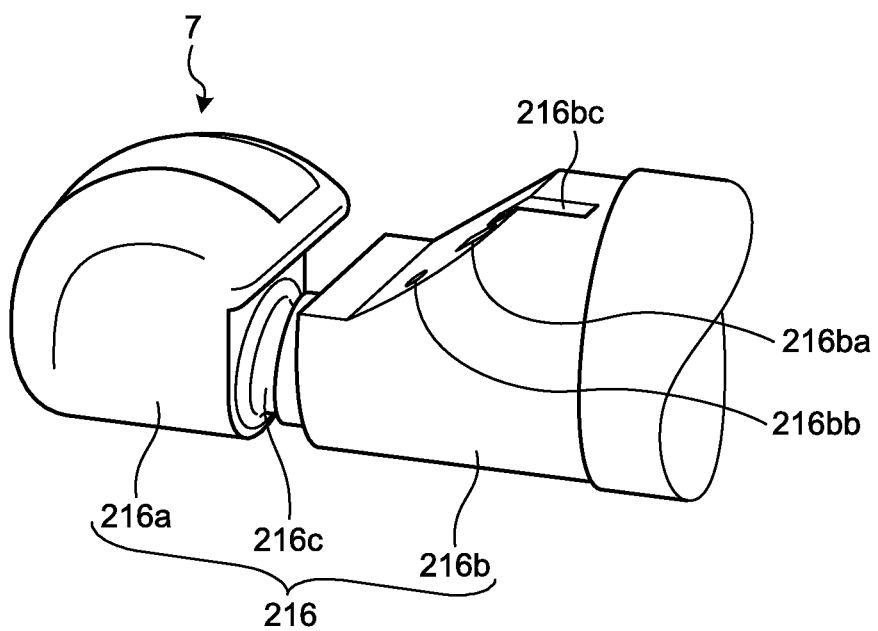
FIG. 10 is a perspective view schematically illustrating a distal end configuration of the insertion portion of the ultrasound endoscope according to the second embodiment.

FIG. 9 is a perspective view schematically illustrating a distal end configuration of an insertion portion of an ultrasound endoscope according to a second embodiment. FIG. 10 is a perspective view schematically illustrating a distal end configuration of the insertion portion of the ultrasound endoscope according to the second embodiment, and is a perspective view of a distal end configuration of the insertion portion that is viewed from an opposite direction to FIG. 9. In the aforementioned first embodiment, the description has been given assuming that, in the distal end portion 211, the ultrasound functional unit 214 and the endoscope functional unit 215 are provided as separate units. Nevertheless, in a distal end portion 216 according to the second embodiment, an ultrasound functional unit 216a and an endoscope functional unit 216b are integrally provided.

As illustrated in FIG. 9, the distal end portion 216 includes the ultrasound functional unit 216a that holds the ultrasound transducer 7, the endoscope functional unit 216b including an observation window 216ba that causes light to enter an imaging optical system that includes an objective lens and the like, and takes in light from the outside, and an illumination window 216bb constituting a part of an illumination optical system that collects illumination light and emits the light to the outside, and a balloon locking portion 216c that is provided between the ultrasound functional unit 216a and the endoscope functional unit 216b to connect the ultrasound functional unit 216a and the endoscope functional unit 216b, and has a groove shape for locking a balloon. In the endoscope functional unit 216b, a processing tool protrusion port 216bc that is communicated with the processing tool insertion path formed in the insertion portion 21, and causes a processing tool to protrude from the distal end of the insertion portion 21 is formed. The endoscope functional unit 216b connects to the ultrasound functional unit 216a at one end, and connects to the curve portion 212 at another end.

Figure 11:
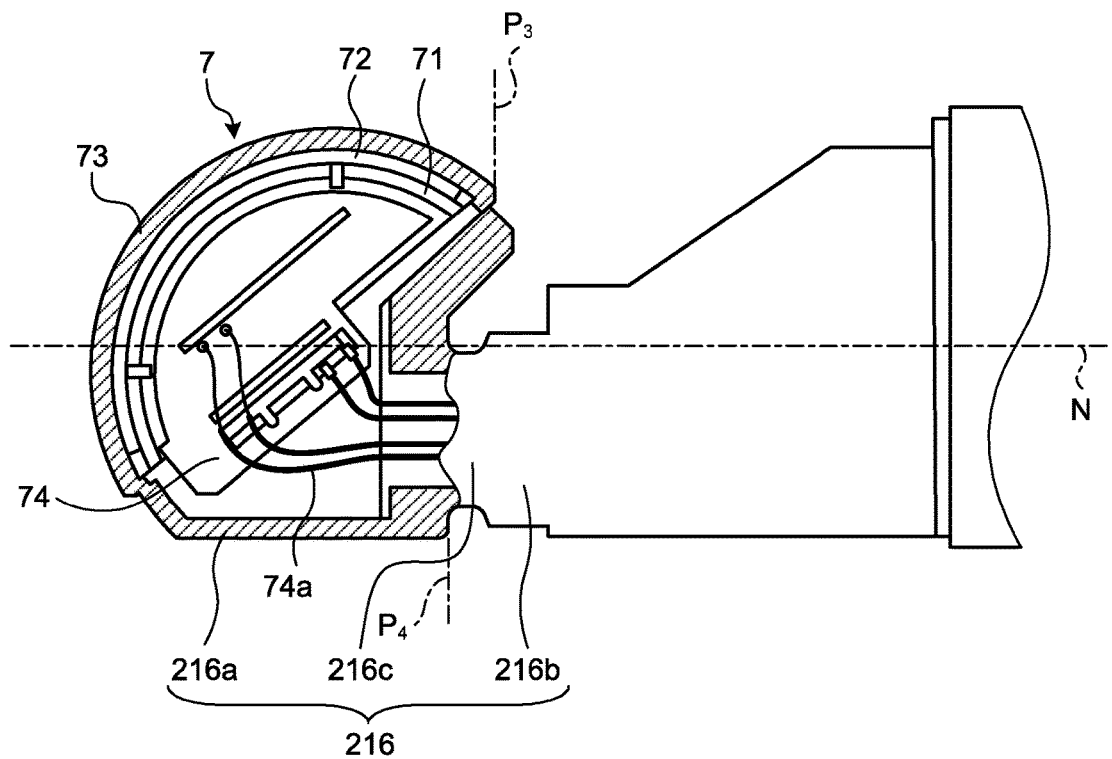
FIG. 11 is a partially-enlarged view schematically illustrating a configuration of an ultrasound functional unit according to the second embodiment.

Subsequently, the arrangement of the ultrasound transducer 7 in the ultrasound functional unit 216a will be described with reference to FIG. 11. FIG. 11 is a partially-enlarged view schematically illustrating a configuration of the ultrasound functional unit according to the second embodiment, and is a partially-enlarged view in which a plane passing through the longitudinal axis N of the insertion portion 21 is assumed to be a cutting plane. As illustrated in FIG. 11, in the longitudinal axis N direction of the insertion portion 21, a plane $P_3$ (first plane) passing through an end portion (first end portion) near the endoscope functional unit 216b of the ultrasound transducer 7 is positioned closer to a proximal end than a plane $P_4$ (second plane) passing through an end portion (second end portion) near the ultrasound functional unit 216a of the balloon locking portion 216c. The plane $P_3$ is perpendicular to the longitudinal axis N of the insertion portion 21.

For example, in the case of increasing a curvature radius of a curved surface of the ultrasound transducer 7 (curved surface passing through distal ends of a plurality of piezoelectric elements) without changing the size and the number of piezoelectric elements, if an end portion on the proximal end side of the ultrasound transducer 7 is extended toward the proximal end side of the insertion portion 21 so as to satisfy a positional relationship with the plane $P_3$ and the plane $P_4$, without elongating an end portion on the distal end side of the ultrasound transducer 7, even if the ultrasound transducer 7 upsizes, the insertion portion 21 can be formed without elongating an extension length in the longitudinal axis direction of the insertion portion 21.

Figure 12:
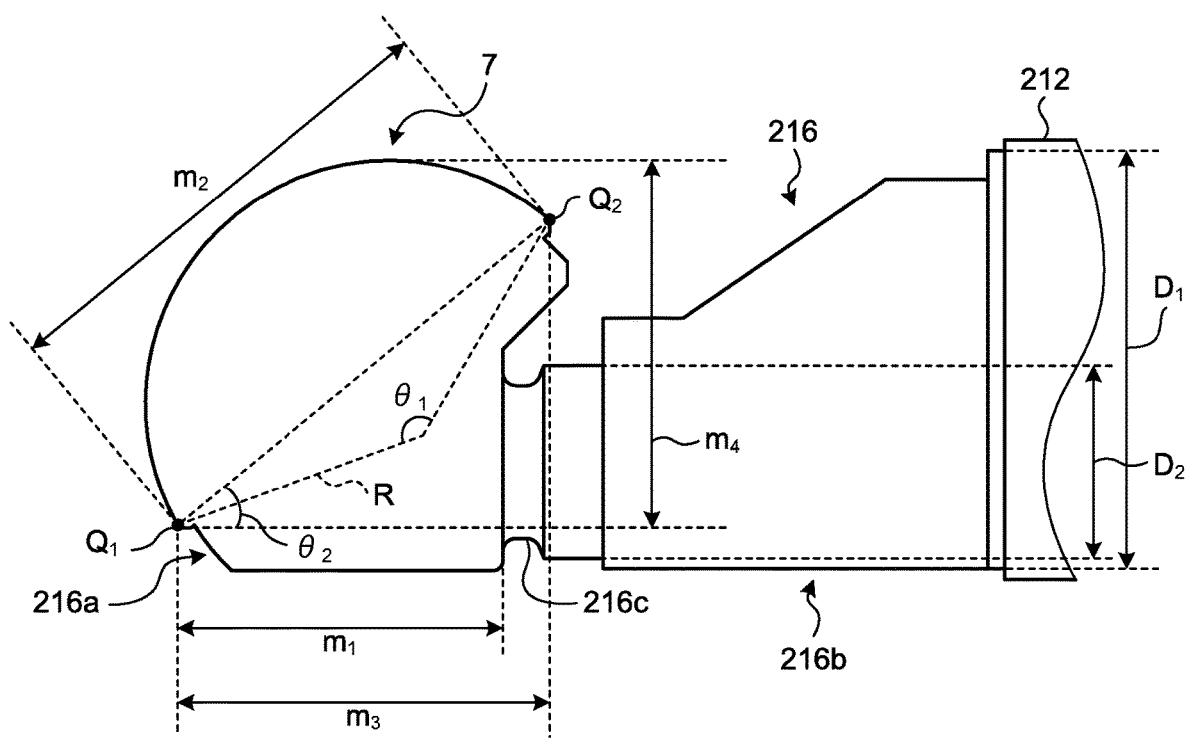
FIG. 12 is a side view schematically illustrating a distal end configuration of the insertion portion of the ultrasound endoscope according to the second embodiment.

FIG. 12 is a side view schematically illustrating a distal end configuration of the insertion portion of the ultrasound endoscope according to the second embodiment, and is a diagram illustrating a relationship between lengths of portions in the distal end portion 216. When a largest diameter of the endoscope functional unit 216b is denoted by $D_1$, a smallest diameter of the endoscope functional unit 216b is denoted by $D_2$, an end portion (third end portion) on a distal end side in an array direction of the piezoelectric elements of the ultrasound transducer 7 is denoted by $Q_1$, an end portion (first end portion) on a proximal end side is denoted by $Q_2$, a distance that is from the end portion $Q_1$ to an end portion (second end portion) on the ultrasound functional unit 216a side of the balloon locking portion 216c, and is a distance (first distance) in the longitudinal axis direction of the insertion portion 21 is denoted by $m_1$, a distance between the end portions $Q_1$ and $Q_2$ is denoted by $m_2$, a distance (second distance) in the longitudinal axis direction of the insertion portion 21 between the end portions $Q_1$ and $Q_2$ is denoted by $m_3$, a distance that is from the end portion $Q_1$ to the end portion of the ultrasound transducer 7, and is the largest distance in a direction perpendicular to the longitudinal axis N direction of the insertion portion 21 is denoted by $m_4$, a curvature radius of the curved surface of the ultrasound transducer 7 (curved surface passing through distal ends of a plurality of piezoelectric elements) is denoted by R, an angle formed by the end portions $Q_1$ and $Q_2$, and the center of curvature of the curved surface of the ultrasound transducer 7 is denoted by $\theta_1$, and an angle formed by a straight line being parallel to the longitudinal axis direction of the insertion portion 21, and a straight line passing through the end portions $Q_1$ and $Q_2$ is denoted by $\theta_2$, relationships represented by the following formulae (1) to (4) are satisfied.

$$m_2 = 2 \times R \sin(\theta_1/2) \quad (1)$$

$$m_3 = m_2 \cos \theta_2 \quad (2)$$

$$m_1 < m_3 \quad (3)$$

$$D_2 < m_4 < D_1 \quad (4)$$

In addition, as in the aforementioned first embodiment, the outer surface of the ultrasound transducer 7 is provided so as not to interfere with the axis (axis $L_1$) extending in an extending direction of the processing tool protruding from the processing tool protrusion port 216bc. Thus, if the ultrasound transducer 7 satisfies the aforementioned positional relationship with the plane $P_3$ and the plane $P_4$, the ultrasound transducer 7 does not interfere with an operation of the processing tool protruding from the processing tool protrusion port 216bc.

In addition, the axis (axis $L_2$) passing through the center of the ultrasound transducer 7 in a direction perpendicular to the longitudinal axis direction of the insertion portion 21, and being parallel to the longitudinal axis direction of the insertion portion 21 is provided to be offset with respect to the axis (axis $L_3$) passing through the center of the observation window 216ba, and being parallel to the longitudinal axis direction of the insertion portion 21. Thus, for example, even if the outer surface of the acoustic lens 73 forms a convex shape along a direction perpendicular to the longitudinal axis direction of the insertion portion 21, the ultrasound transducer 7 does not interfere with light entering the observation window 216ba.

In addition, the outer surface of the ultrasound transducer 7 does not interfere with the optical axis (optical axis $L_4$) of light entering the observation window 216ba, and the optical axis (optical axis $L_5$) of illumination light emitted by the illumination window 216bb constituting a part of the illumination optical system. Thus, if the ultrasound transducer 7 satisfies the aforementioned positional relationship with the plane $P_3$ and the plane $P_4$, the ultrasound transducer 7 does not interfere with observation light entering the observation optical system, and illumination light emitted from the illumination window 216bb.

According to the second embodiment described above, the plane $P_3$ passes, in the longitudinal axis direction of the insertion portion 21, through an end portion near the endoscope functional unit 216b of the ultrasound transducer 7 and is perpendicular to the longitudinal axis of the insertion portion 21. The plane $P_3$ is positioned closer to the proximal end than the plane $P_4$ passing through an end portion of the balloon locking portion 216c near the ultrasound functional unit 216a. Thus, a curvature radius of the ultrasound transducer 7 can be increased without elongating an extension length of the ultrasound transducer 7, and without causing upsizing.

In addition, an ultrasound miniature probe not having an optical system and having a thin diameter may be applied as the ultrasound endoscope. The ultrasound miniature probe is normally inserted into a biliary tract, biliary duct, pancreas duct, trachea, bronchus, urethra, or ureter, and is used when their adjacent organs (pancreas, lung, glandula prostatica, urinary bladder, lymph nodes, etc.) are observed.

In addition, an external ultrasound probe that emits ultrasound waves from a body surface of a subject may be applied as an ultrasound endoscope. The external ultrasound probe is normally used when abdominal organs (liver, cholecystis, urinary bladder), breast (in particular, glandula mammaria), and glandula thyreoidea are observed.

As described above, an ultrasound endoscope according to the present disclosure is useful in increasing a curvature radius of an ultrasound transducer without causing upsizing.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound endoscope, comprising:
   an insertion portion extending along a longitudinal axis;
   an ultrasound transducer including a plurality of piezoelectric elements, the ultrasound transducer being configured to transmit and receive an ultrasound wave, at least a portion of the plurality of piezoelectric elements extending in a longitudinal axis direction; and
   an endoscope functional portion provided at a distal end of the insertion portion, the endoscope functional portion comprising:
     a connector connected to the ultrasound transducer; and
     an objective lens system comprising an objective lens,
   wherein the ultrasound transducer being disposed in a body, the body having a protrusion extending in the longitudinal axis direction, the connector having a hole extending in the longitudinal axis direction, the protrusion mating with the hole to attach the body having the ultrasound transducer to the distal end of the insertion portion; and
   a proximal-most end of a portion of the ultrasound transducer that is outside of the hole is positioned proximally relative to a distal-most end of the hole of the connector.

2. The ultrasound endoscope according to claim 1, wherein the connector is configured to detach the body having the ultrasound transducer from the endoscope functional portion.

3. The ultrasound endoscope according to claim 1, wherein the body further having a projection, the projection protrudes in a direction that intersects the longitudinal axis, the endoscope functional unit further having a recess, the recess being recessed in the direction, and the projection being disposed within the recess to suppress rotation of the body having the ultrasound transducer around an axis that is parallel to the longitudinal axis, with respect to the endoscope functional portion.

4. The ultrasound endoscope according to claim 1, wherein all portions of ultrasound transducer are outside the hole.

5. The ultrasound endoscope according to claim 1, wherein
   the objective lens having an optical axis; and
   an extension of the optical axis from the objective lens towards the ultrasound transducer does not interfere with any portions of an outer surface of the ultrasound transducer.

6. The ultrasound endoscope according to claim 1, wherein
   the endoscope functional portion comprising an opening, the opening being configured to protrude a processing tool from the opening along a tool axis; and
   an extension of the tool axis from the opening towards the ultrasound transducer does not interfere with any portions of an outer surface of the ultrasound transducer.

7. The ultrasound endoscope according to claim 1, wherein the ultrasound transducer further comprising an acoustic matching layer in contact with the plurality of piezoelectric elements.

8. The ultrasound endoscope according to claim 7, wherein the ultrasound transducer further comprising an acoustic lens covering the acoustic matching layer.

9. The ultrasound endoscope according to claim 1, wherein the hole having an opening formed in a plane perpendicular to the longitudinal axis.

10. The ultrasound endoscope according to claim 1, wherein the portion of the ultrasound transducer that is outside the hole overlaps with a portion of the hole in a radial direction.

11. An insertion portion for use with an ultrasound endoscope, the insertion portion comprising:
    an ultrasound transducer including a plurality of piezoelectric elements, the ultrasound transducer being configured to transmit and receive an ultrasound wave, at least a portion of the plurality of piezoelectric elements extending in a longitudinal axis direction; and
    an endoscope functional portion provided at a distal end of the insertion portion, the endoscope functional portion comprising:
      a connector connected to the ultrasound transducer; and
      an objective lens system comprising an objective lens,
    wherein the ultrasound transducer being disposed in a body, the body having a protrusion extending in the longitudinal axis direction, the connector having a hole extending in the longitudinal axis direction, the protrusion mating with the hole to attach the body having the ultrasound transducer to the distal end of the insertion portion; and
    a proximal-most end of a portion of the ultrasound transducer that is outside of the hole is positioned proximally relative to a distal-most end of the hole of the connector.

12. The insertion portion according to claim 11, wherein all portions of ultrasound transducer are outside the hole.

13. The insertion portion according to claim 11, wherein
    the objective lens having an optical axis; and
    an extension of the optical axis from the objective lens towards the ultrasound transducer does not interfere with any portions of an outer surface of the ultrasound transducer.

14. The insertion portion according to claim 11, wherein
the endoscope functional portion comprising an opening,
  the opening being configured to protrude a processing tool from the opening along a tool axis; and
  an extension of the tool axis from the opening towards the ultrasound transducer does not interfere with any portions of an outer surface of the ultrasound transducer.

15. The insertion portion according to claim 11, wherein the ultrasound transducer further comprising an acoustic matching layer in contact with the plurality of piezoelectric elements.

16. The insertion portion according to claim 15, wherein the ultrasound transducer further comprising an acoustic lens covering the acoustic matching layer.

17. The insertion portion according to claim 11, wherein the hole having an opening formed in a plane perpendicular to the longitudinal axis.

18. The insertion portion according to claim 11, wherein the portion of the ultrasound transducer that is outside the hole overlaps with a portion of the hole in a radial direction.

* * * * *